(12) United States Patent
Robin et al.

(10) Patent No.: US 6,348,633 B1
(45) Date of Patent: Feb. 19, 2002

(54) BROMINE-CONTAINING 1,2-BIS(PHENYL) DIFLUOROMETHANES AND METHOD OF IMPARTING FLAME RETARDANCY TO FLAMMABLE MATERIALS

(75) Inventors: Mark L. Robin, West Lafayette; Charles J. Mazac, Zionsville; Leonard J. Chyall, Lafayette, all of IN (US); Paul Kleindl, Madison, WI (US)

(73) Assignee: PCBU Services, Inc., Wilmington, DE (US)

( * ) Notice: Subject to any disclaimer, the term of this patent is extended or adjusted under 35 U.S.C. 154(b) by 0 days.

(21) Appl. No.: 09/806,745

(22) PCT Filed: Oct. 5, 1999

(86) PCT No.: PCT/US99/22866

§ 371 Date: Jul. 2, 2001

§ 102(e) Date: Jul. 2, 2001

(87) PCT Pub. No.: WO00/20364

PCT Pub. Date: Apr. 13, 2000

Related U.S. Application Data

(60) Provisional application No. 60/103,335, filed on Oct. 7, 1998.

(51) Int. Cl.$^7$ .......................... C07C 19/08; C07C 25/13; C08K 5/02
(52) U.S. Cl. ........................ 570/129; 570/149; 523/462; 524/462
(58) Field of Search ................................ 570/147, 129; 524/462; 523/462

(56) References Cited

U.S. PATENT DOCUMENTS 4,075,164 A * 2/1978 Mark
4,423,259 A * 12/1983 Kobayashi et al.
6,242,654 B1 * 6/2001 Goto et al.

* cited by examiner

*Primary Examiner*—Alan Siegel
(74) *Attorney, Agent, or Firm*—Marshall, Gerstein, & Borun

(57) ABSTRACT

Bromine containing 1,2-bis(phenyl)difluoromethane derivatives, a method for their preparation and their use in flame retardant compositions.

25 Claims, No Drawings

BROMINE-CONTAINING 1,2-BIS(PHENYL) DIFLUOROMETHANES AND METHOD OF IMPARTING FLAME RETARDANCY TO FLAMMABLE MATERIALS

CROSS-REFERENCE TO RELATED APPLICATION

This application is a continuation-in-part of U.S. Provisional Patent Application No. 60/103,335 filed Oct. 7, 1998.

FIELD OF THE INVENTION

The present invention relates to bromine-containing 1,2-bis(phenyl)difluoromethanes of the formula:

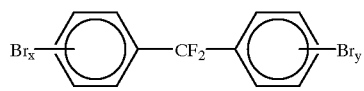

(I)

wherein x=1–5, and y=0–5. Also disclosed is a method for the preparation of these compounds. The compounds of formula I are useful as intermediates in producing compounds exhibiting pharmaceutical or agricultural activity, and the compounds of formula I are useful as flame retardants.

BACKGROUND OF THE INVENTION

Decabromodiphenyl alkanes ($C_{1-10}$), such as decabromodiphenyl methane and decabromodiphenyl ethane are known compounds that are useful as flame retardants, as disclosed in Hussain U.S. Pat. No. 5,008,477. The compounds are prepared by brominating diphenyl alkane, in the presence of a bromination catalyst such as $AlCl_3$ and/or $AlBr_3$, at a temperature of about 50° C. to about 60° C., wherein the alkane group has 1–10 carbon atoms. It has been found, in accordance with the present invention, that the above-defined bromine-containing 1,2-bis(phenyl) difluoromethylene compounds can be prepared and exhibit improved flame retardancy to flammable materials.

SUMMARY OF THE INVENTION

The novel compounds in accordance with the present invention have the general formula

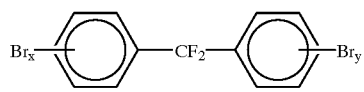

(I)

where:
x is equal to 1–5, y is equal to 0–5; and x=1, y=1 (for o,o'; o,m'; o,p'; m,m'; and m,p' only). In the case of x=1 and y=0, the para compound is known, but is novel as a flame retardant. Similarly, for x=1, y=1, the para, para' compound is known, but is novel as a flame retardant.

The compounds of formula I can be used as synthesis intermediates for the preparation of agricultural and pharmaceutical compounds, and can also be used as flame retardants.

DETAILED DESCRIPTION OF THE INVENTION

The novel compounds in accordance with the present invention have the general formula:

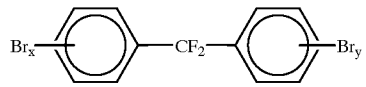

(I)

where:

x is equal to 1–5, and y is equal to 0–5; and where x=1, and y=0, o and m only (excluding para bromo); and where x=1, and y=1, o,o'; o,m'; o,p'; m,m'; and m,p' (excluding para, para'), the excluded compounds are known in the art per se, but not as flame retardants).

The novel compounds are any of the following compounds:

$C_{13}H_9F_2Br$

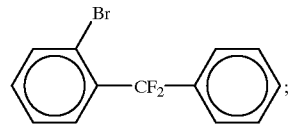

$C_{13}H_8F_2Br_2$

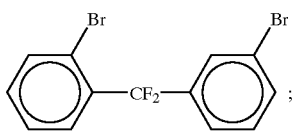

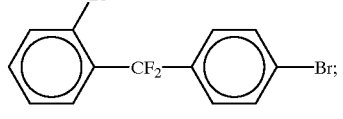

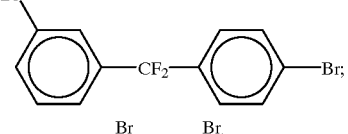

$C_{13}H_7F_2Br_3$

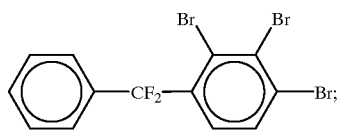

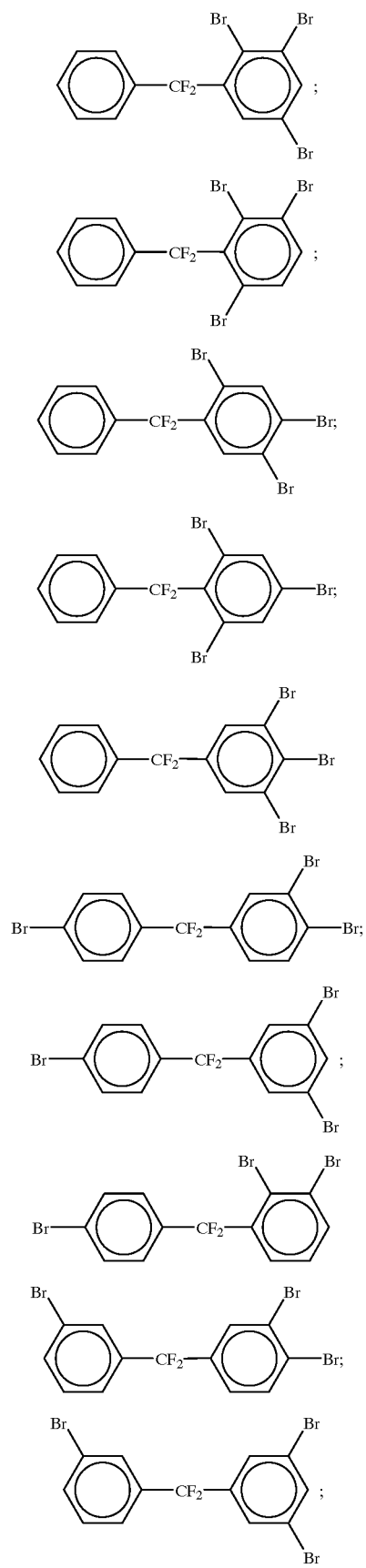
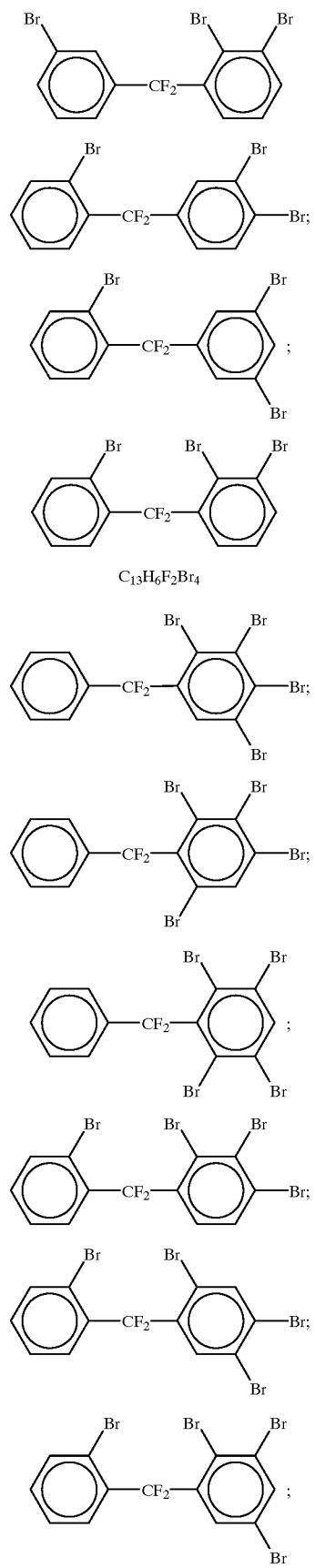
$C_{13}H_6F_2Br_4$

-continued

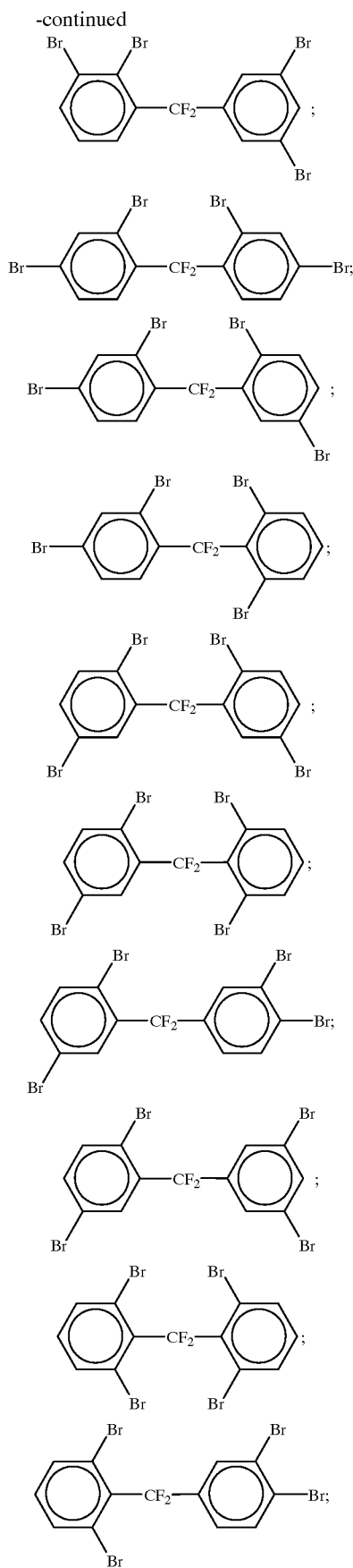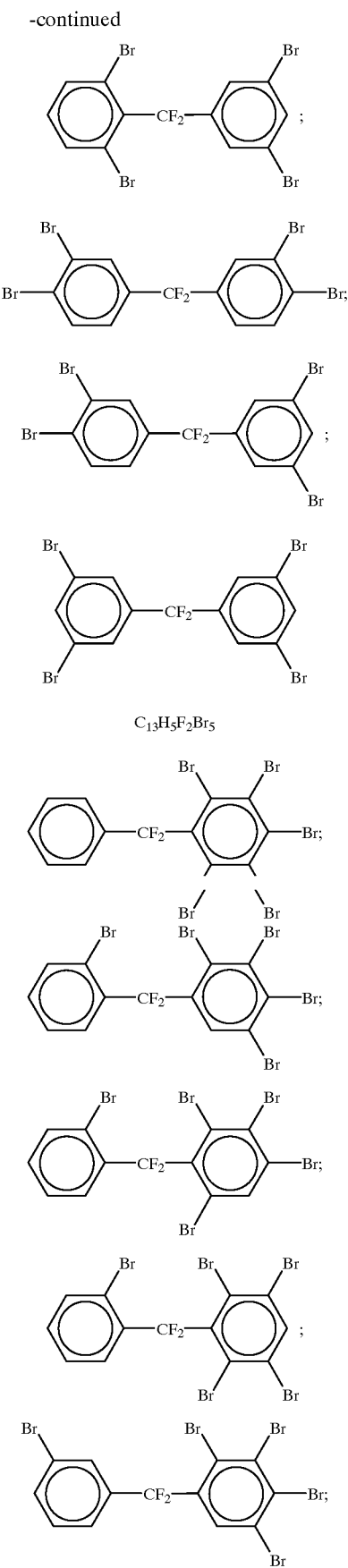

-continued
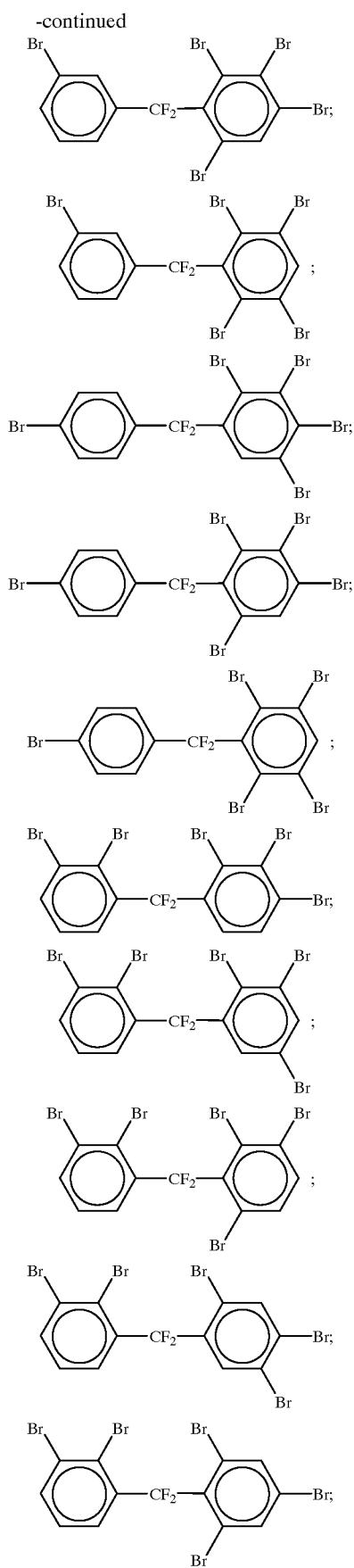
-continued
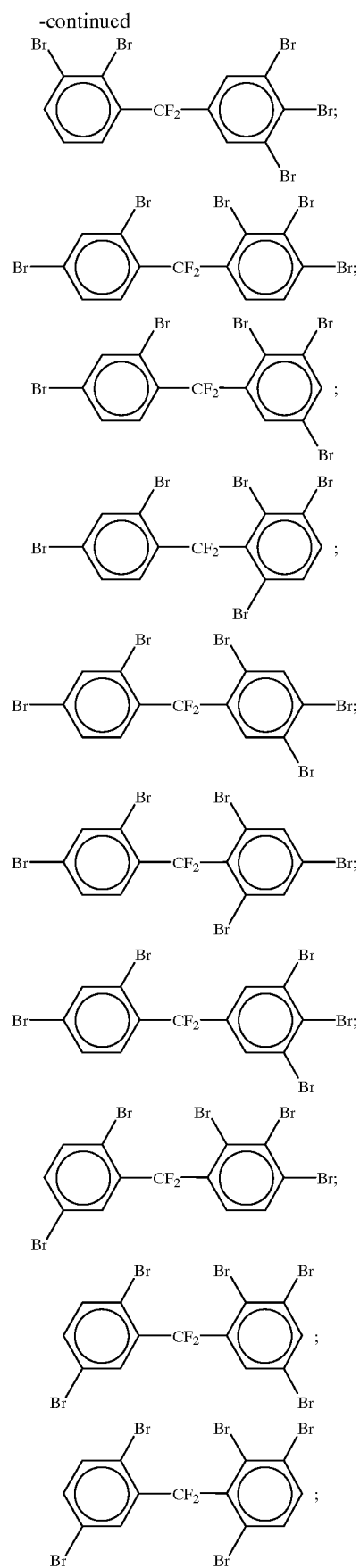

-continued

-continued
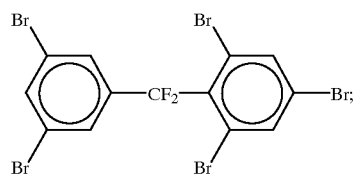
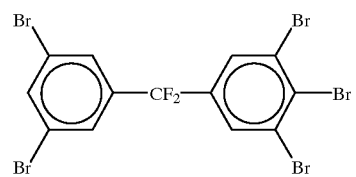
$C_{13}H_4F_2Br_6$
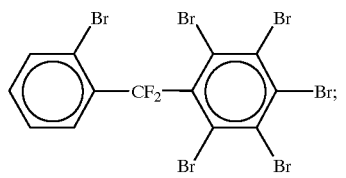
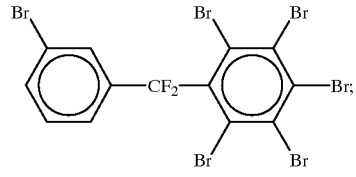
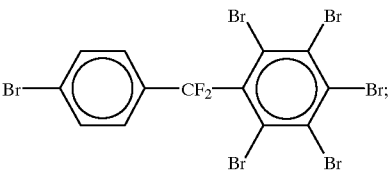
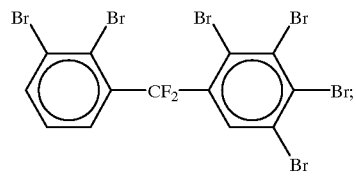
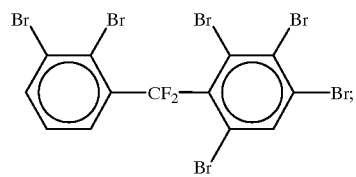
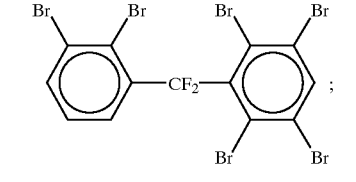
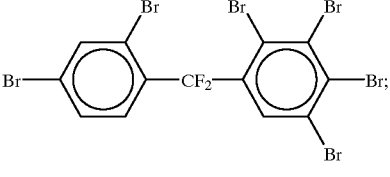
-continued
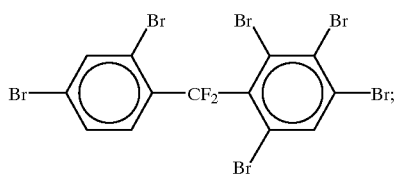
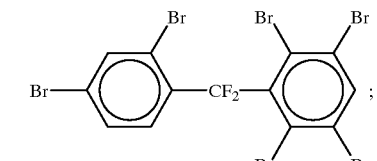
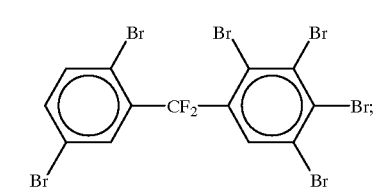
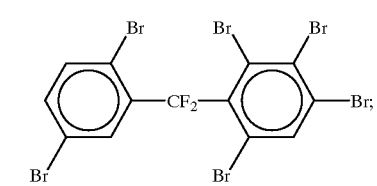
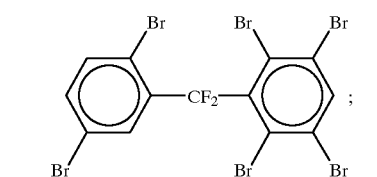
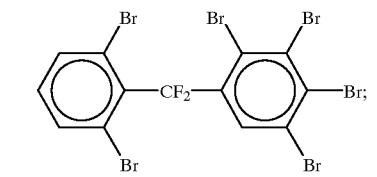
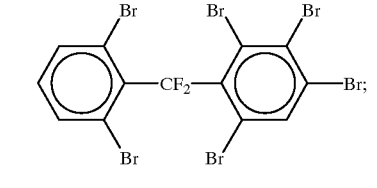
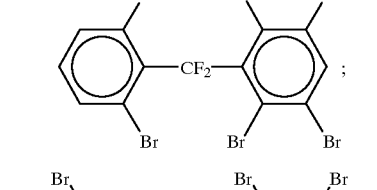
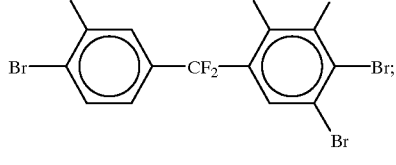

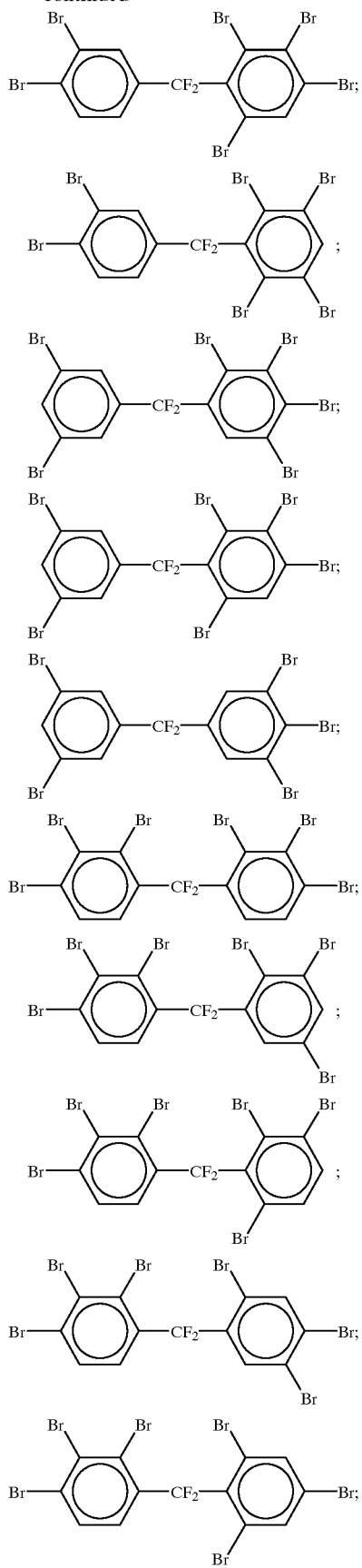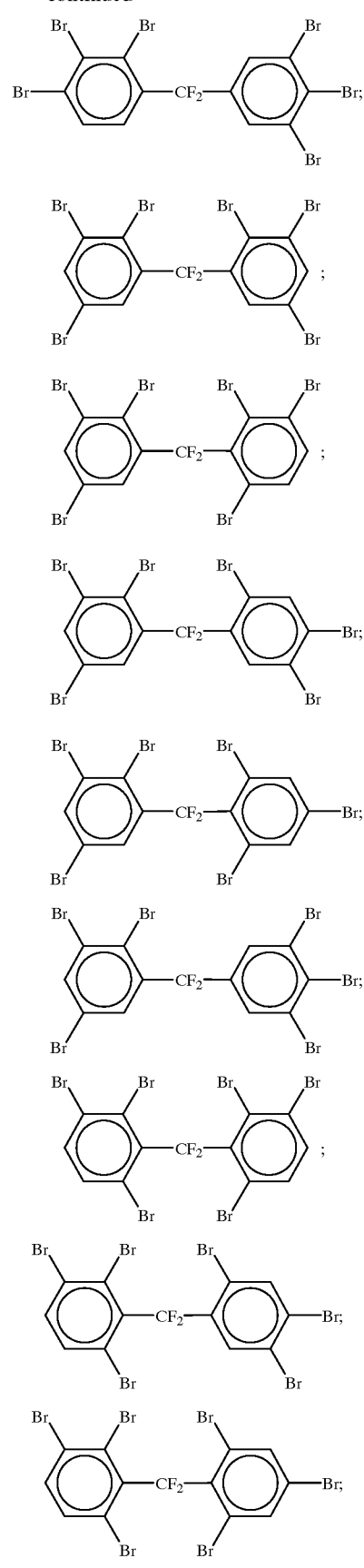

-continued
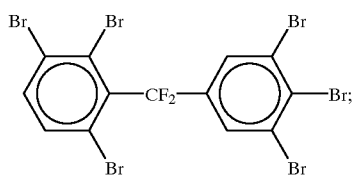
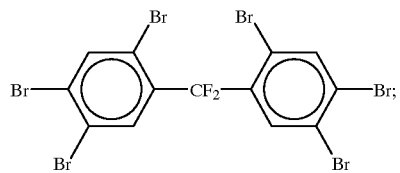
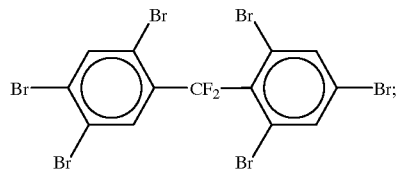
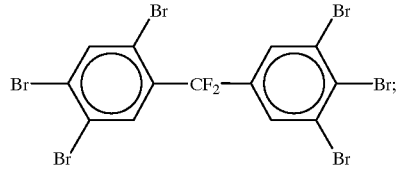
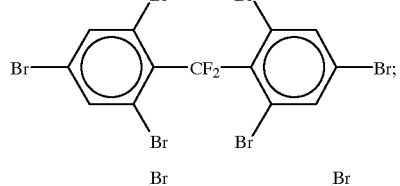
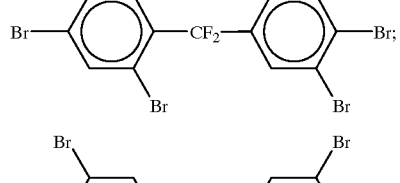
$C_{13}H_3F_2Br_7$
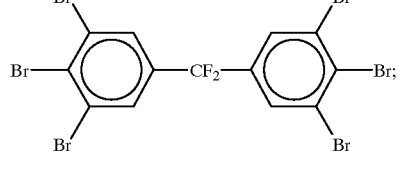
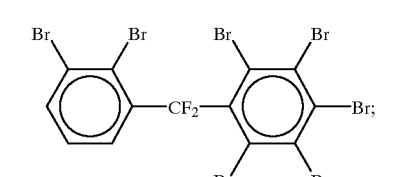
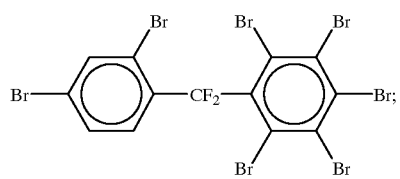
-continued
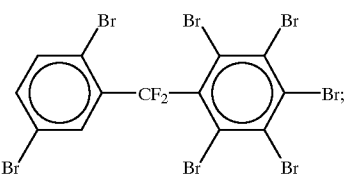
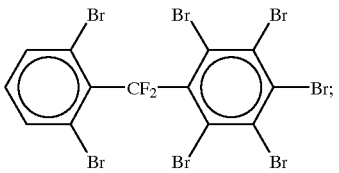
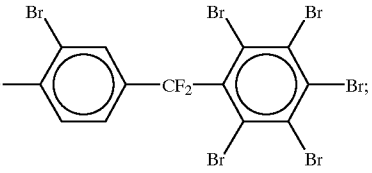
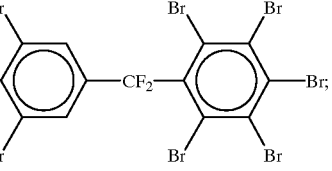
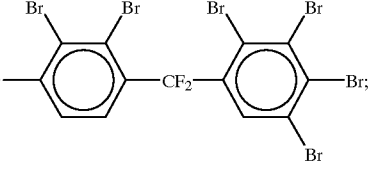
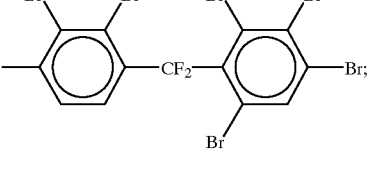
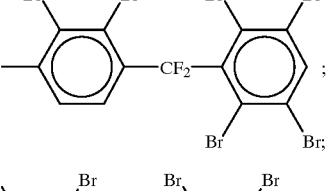
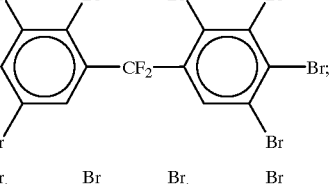
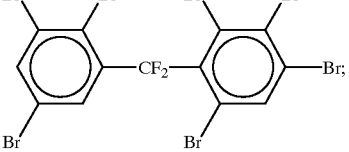

-continued
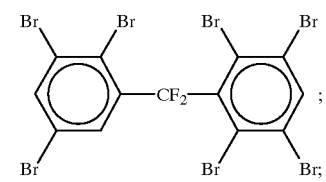
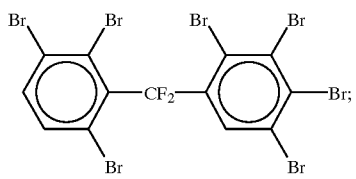
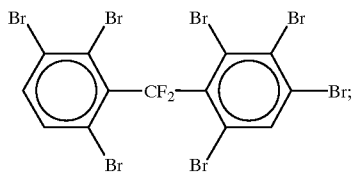
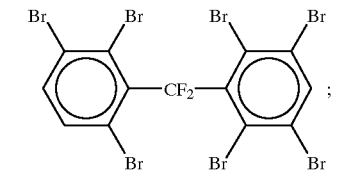
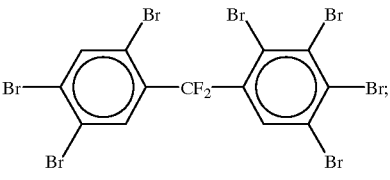
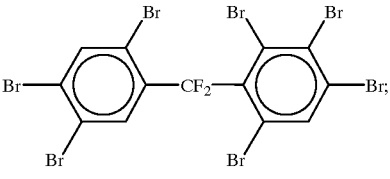
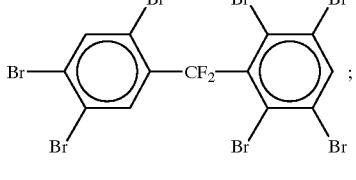
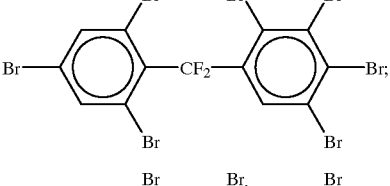
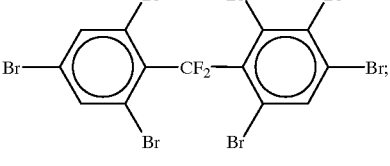
-continued
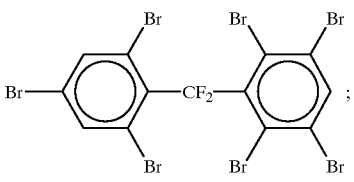
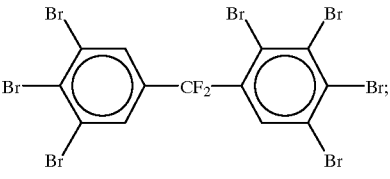
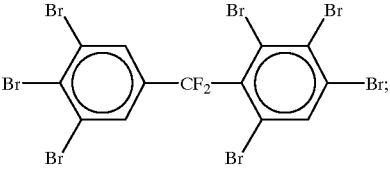
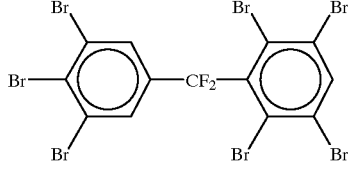
$C_{13}H_2F_2Br_8$
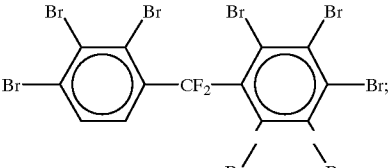
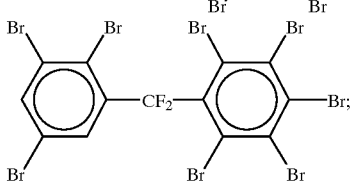
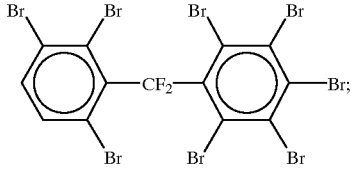
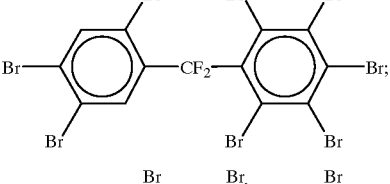
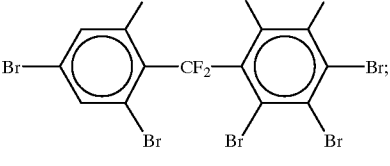

-continued

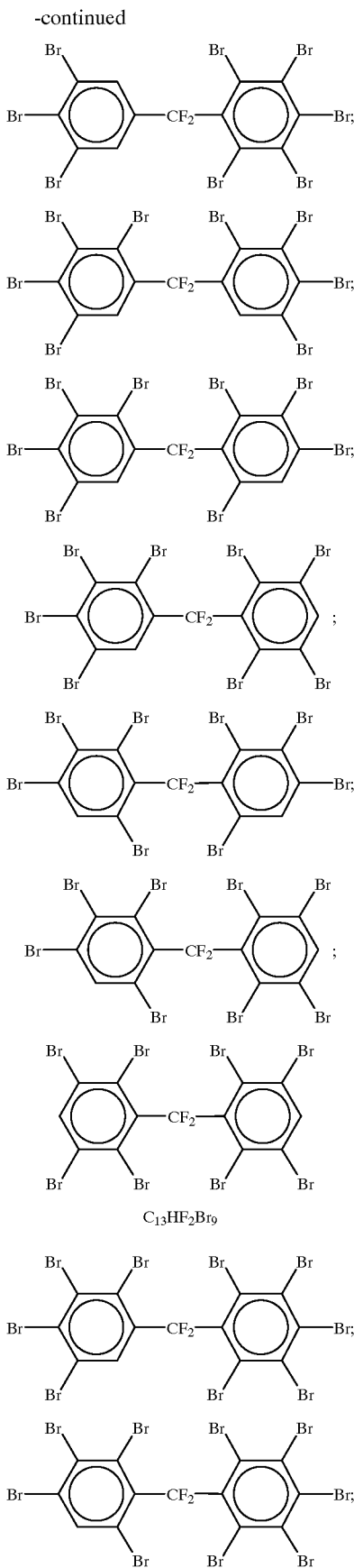

C₁₃HF₂Br₉

-continued

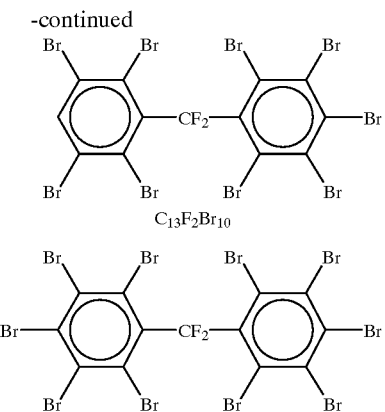

C₁₃F₂Br₁₀

The compounds of formula I may be prepared in a number of ways. For example, the compounds may be prepared via the reaction of 1,2-bis(phenyl)difluoromethane with a bromination agent, such as elemental bromine in fuming sulfuric acid:

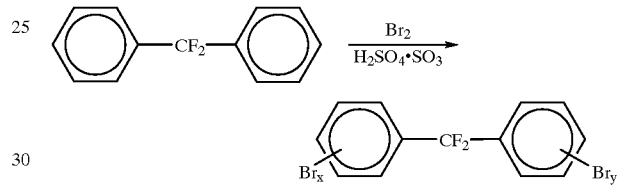

wherein x=1–5; and y=0–5.

The amount of bromine reacted with the 1,2-bis(phenyl) difluoromethane reactant is readily controlled by adjusting the molar ratio of bromine to 1,2-bis(phenyl) difluoromethane. Excess bromine favors the formation of the more highly brominated compounds of the present invention, whereas lower amounts of bromine favor the production of the less heavily brominated compounds of the present invention.

Alternatively, as is taught in the prior art, different bromination agents may be employed, for example, elemental bromine in the presence of a Lewis acid, or N-bromo compounds such as N-bromosuccinimide and dibromodimethylhydantoin.

The 1,2-bis(phenyl)difluoromethane precursor may be prepared via the reaction of benzophenone with a fluorination agent, such as SF₄, diethylaminosulfur trifluoride (DAST), alkylsulfur trifluorides or arylsulfur trifluorides. Alternatively, benzophenone can be transformed to the corresponding hydrazone or 1,3-dithiolane followed by treatment with a fluorination agent such as hydrogen fluoride (HF), polyvinylpyridinium poly(hydrogen fluoride) [PVPPHF], pyridinium poly(hydrogen fluoride) [PPHF], and an N-bromo compound, such as N-bromosuccinimide or dibromdimethyl hydantoin. Preferred is PVPPHF or PPHF and an N-bromo compound, such as N-bromosuccinimide or dibromdimethyl hydantoin.

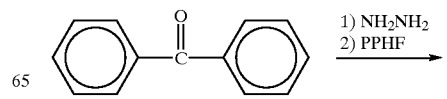

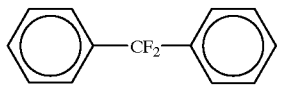

All of the above-mentioned compounds are useful as flame retardants for use with any flammable material, as well as the following compounds:

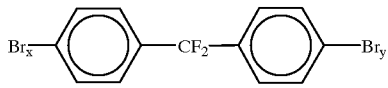

where x=0 or 1 and y=0 or 1 and x+y=1–2.

When used as a flame retardant for a flammable material, the bromine-containing 1,2-bis(phenyl)difluoromethane should be incorporated into or onto the flammable material in an amount sufficient to obtain the desired flame retardancy, which varies with the particular flammable material in which the compound(s) is incorporated. In general, the amount of compound(s) incorporated into the flammable material is in the range of about 2% to about 50% by weight of flammable material, preferably about 5% to about 30%, based on the weight of flammable material.

The bromine-containing 1,2-bis(phenyl)difluoromethanes of the present invention are useful for flame retardation of any flammable material, including monomers and oligomers, but are particularly advantageous for flame retarding thermoplastic and thermosetting polymers and copolymers. Examples include polyolefins, polyurethanes, polyamides, polyimides, polycarbonates, polyethers, polyesters, epoxy resins, polyphenols, and elastomers, such as natural rubber, butyl rubber, and polysilanes. The oligomers and polymers may be cross-linked or non cross-linked and may contain typical additives, such as plasticizers, stabilizers, antioxidants, fillers, pigments and the like. The flame retardant compounds of the present invention can be compounded into the flammable material at any stage of processing, e.g., added to the monomer or oligomer prior to, during, or after polymerization, or during extrusion, melt blending, or molding of the flammable material, e.g., polymer.

The following examples are provided for illustrative purposes only and should not be construed to limit the scope of the invention.

EXAMPLE 1

Preparation of 1,2-bis(phenyl)difluoromethane

To a polyethylene bottle containing a suspension of N-bromosuccinimide (1.2 g, 6.6 mmol) and polyvinylpyridinium poly(hydrogen fluoride) [1.9 g, 59% w/w HF] in dry methylene chloride (10 mL) maintained at −40° C. was added dropwise a solution of benzophenone hydrazone (0.52 g, 2.6 mmol) in methylene chloride (5 mL). The mixture was stirred and allowed to warm to room temperature over the course of 30 minutes and then stirred at room temperature for 2 hours. The mixture was then filtered and the wet cake washed with sodium bicarbonate solution and water, then dried over magnesium sulfate and filtered. The methylene chloride was removed under reduced pressure and the residue was redissolved in pentane which gave a precipitate that was removed by filtration. The filtrate was concentrated to yield 0.4 g of crude 1,2-bis(phenyl)difluoromethane. The crude product was purified via column chromatography to yield 0.30 g of a clear oil, shown to be the desired product by nuclear magnetic resonance NMR), Fourier Transform Infra Red (FTIR) and gas chromatography/mass spectrometry (GC/MS) analysis.

EXAMPLE 2

Preparation of 1,2-bis(pentabromophenyl) difluoromethane

To a flask charged with 1,2-bis(phenyl)difluoromethane (1.0 g, 5.00 mmol), which is as described in Example 1, is added 34.7 g of 65% fuming sulfuric acid. Bromine (7.87 g, 49.5 mmol) is then added dropwise over a period of 30 minutes. The solution is then stirred for 4.5 hours at room temperature, and the reaction mixture is poured onto ice and the resulting mixture is then filtered. The recovered solid is washed with several portions of water and methylene chloride and can be identified by nuclear magnetic resonance (NMR), mass spectrometry (MS), Fourier Transform infra Red (FTIR), and bromine content analysis as 1,2-bis(pentabromo-phenyl)difluoromethane.

EXAMPLE 3

Employing the method of Example 2, but with lower bromine to 1,2-bis(phenyl)difluoromethiane molar ratios (0.5–9 to 1) products of the current invention containing from 3 to 9 bromine atoms are readily prepared.

What is claimed is:

1. Bromine-containing 1,2-bis(phenyl)difluoromethanes of the formula:

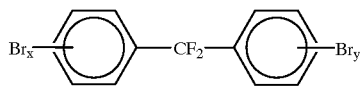

where x=1–5, and y=0–5; and wherein x=1 and y=0, ortho and meta only; and wherein x=1 and y=1, ortho, ortho'; ortho, meta'; ortho, para'; meta, meta'; and meta, para'.

2. A bromine-containing 1,2-bis(phenyl)difluoromethane according to claim 1, having a formula selected from the group consisting of

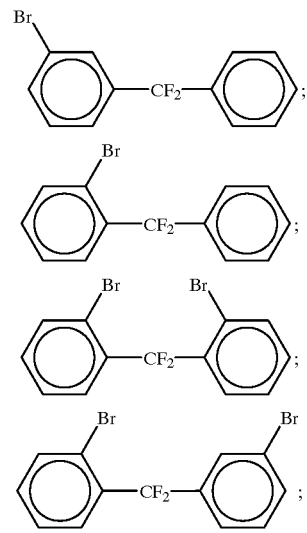

-continued

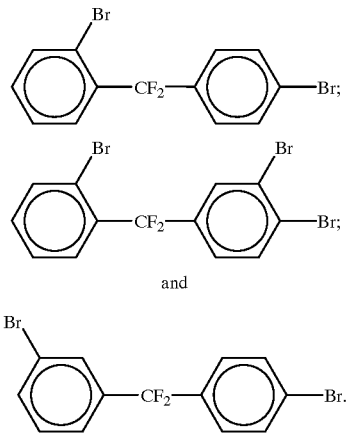

3. A bromine-containing 1,2-bis(phenyl)difluoromethane according to claim 1, having the formula:

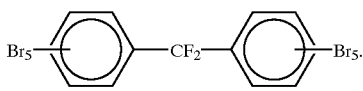

4. A bromineontaining 1,2-bis(phenyl)difluoromethane according to claim 1, of the formula

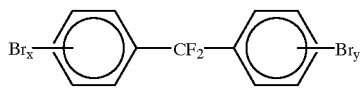

wherein x=2–5 and y=2–5.

5. A method of providing flame retardancy to a flammable material comprising incorporating into said flammable material a flame retardant-effective amount of a bromine-containing 1,2-bis(phenyl)difluoromethane of the formula:

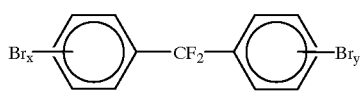

wherein x=1–5, and y=0–5.

6. A method in accordance with claim 5, wherein the flammable material comprises a polymer.

7. A method in accordance with claim 6, wherein the polymer is a polymer or copolymer selected from the group consisting of polyolefins, polyurethanes, polyamides, polyimides, polycarbonates, polyethers, epoxy resins, polyphenols, elastomers, polysiloxanes, and mixtures thereof.

8. A method in accordance with claim 5, wherein the bromine-containing 1,2-bis(phenyl)difluoromethane is incorporated into the flammable material in an amount in the range of about 2% to about 50% by weight, based on the weight of the flammable material.

9. A method in accordance with claim 5, wherein the bromine-containing 1,2-bis(phenyl)difluoromethane is incorporated into the flammable material in an amount in the range of about 5% to about 30% by weight, based on the weight of the flammable material.

10. A method of making a brominecontaining 1,2-bis(phenyl)difluoromethane of the formula:

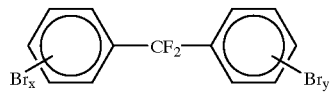

wherein x=1–5 and y=0–5; wherein x=1 and y=0, ortho and meta only; and wherein x=1 and y=1, ortho, ortho'; ortho, meta'; ortho, para'; meta, meta'; and meta, para', comprising brominating 1,2-bis(phenyl)difluoromethane by reaction of the 1,2-bis(phenyl)difluoromethane with a bromination agent.

11. A method in accordance with claim 10, wherein the 1,2-bis(phenyl)difluoromethane is brominated with a bromination agent selected from the group consisting of elemental bromine, N-bromosuccinimide, dibromodimethylhydantoin, and mixtures thereof.

12. A method in accordance with claim 11, wherein the bromination agent is elemental bromine.

13. A method in accordance with claim 12, wherein the bromine is combined with a Lewis acid for contact and reaction with the 1,2-bis(phenyl)difluoromethane.

14. A method in accordance with claim 10, further including the step of forming 1,2-bis(phenyl)difluoromethane by fluorinating benzophenone with a fluorination agent.

15. A method in accordance with claim 14, wherein the fluorination agent is selected from the group consisting of $SF_4$, diethylaminosulfur trifluoride, and mixtures thereof.

16. A method in accordance with claim 10, wherein the bromination agent is added to the 1,2-bis(phenyl)difluoromethane in a molar ratio in the range of 1 to 20 moles of bromination agent per mole of 1,2-bis(phenyl)difluoromethane.

17. A method in accordance with claim 16, wherein the 1,2-bis(phenyl)difluoromethane is formed by contacting benzophenone with 0.2 to 2 moles of fluorination agent per mole of benzophenone.

18. A method in accordance with claim 17, wherein the fluorination agent is diethylaminosulfar trifluoride.

19. A method in accordance with claim 18, wherein the diethylaminosulfur trifluoride is dissolved in an organic solvent.

20. A method in accordance with claim 19, wherein the organic solvent is carbon tetrachloride.

21. A method in accordance with claim 10, further including the step of forming 1,2-bis(phenyl)difluoromethane by first transforming benzophenone to a compound selected from the group consisting of the corresponding hydrazone or 1,3-dithiolane followed by treatment of the hydrazone or 1,3-dithiolane with a fluorinating agent and an N-bromo compound.

22. A method in accordance with claim 21, wherein the benzophenone is transformed to the 1,2-bis(phenyl)difluoromethane by reaction with hydrazine.

23. A method in accordance with claim 21, wherein the benzophenone is transformed to the 1,2-bisnphenyl)difluoromethane by reaction with 1,2-ethanedithiol.

24. A method in accordance with claim 21, wherein the fluorinating agent is selected from the group consisting of hydrogen fluoride, polypyridinium poly(hydrogen fluoride), polyvinylpyridinium poly(hydrogen fluoride), and mixtures thereof.

25. A method in accordance with claim 21, wherein the N-bromo compound is selected from the group consisting of N-bromosuccminide, dibromodimethylhydantoin, and mixtures thereof.

* * * * *